United States Patent

Randolph et al.

[11] Patent Number: 6,114,593
[45] Date of Patent: Sep. 5, 2000

[54] METHOD FOR REDUCING ORGANIC FLUORIDE LEVELS IN HYDROCARBONS

[75] Inventors: Bruce B. Randolph, Bartlesville, Okla.; Kenneth Charles Hoover, New Hartford, N.Y.

[73] Assignee: Phillips Petroleum Company, Bartlesville, Okla.

[21] Appl. No.: 09/238,244

[22] Filed: Jan. 27, 1999

[51] Int. Cl.[7] .............................. C07C 2/56; C07C 7/10; C07C 7/17; C07C 7/00; C10G 17/00

[52] U.S. Cl. .......................... 585/712; 585/842; 585/860; 585/861; 585/862; 585/864; 585/857; 208/262.1

[58] Field of Search .................... 208/262.1; 585/842, 585/860, 861, 862, 864, 857, 712

[56] References Cited

U.S. PATENT DOCUMENTS

| | | | |
|---|---|---|---|
| 3,204,011 | 8/1965 | Hettick et al. | 260/683.42 |
| 5,498,818 | 3/1996 | Randolph et al. | 585/723 |
| 5,654,251 | 8/1997 | Abbott et al. | 502/216 |
| 5,689,030 | 11/1997 | Randolph | 585/724 |

*Primary Examiner*—Jacqueline V. Howard
*Assistant Examiner*—Thuan D. Dang
*Attorney, Agent, or Firm*—Jeffrey R. Anderson

[57] ABSTRACT

A system and/or process for decreasing the level of at least one organic fluoride present in a hydrocarbon mixture by first passing the hydrocarbon mixture to an eductor and educting into the hydrocarbon mixture a catalyst comprising a volatility reducing additive and hydrofluoric acid to produce a hydrocarbon-catalyst mixture, permitting the hydrocarbon-catalyst mixture to undergo a phase separation to produce a hydrocarbon phase having a lower concentration of at least one organic fluoride than the hydrocarbon mixture and to produce a catalyst phase, and withdrawing at least a portion of the hydrocarbon phase to thereby form a hydrocarbon product stream, are disclosed. In an alternate embodiment, a system and/or process for controlling the concentration of at least one organic fluoride and/or the RON of the hydrocarbon mixture by adjusting the amount of volatility reducing additive present in the catalyst are disclosed.

5 Claims, 1 Drawing Sheet

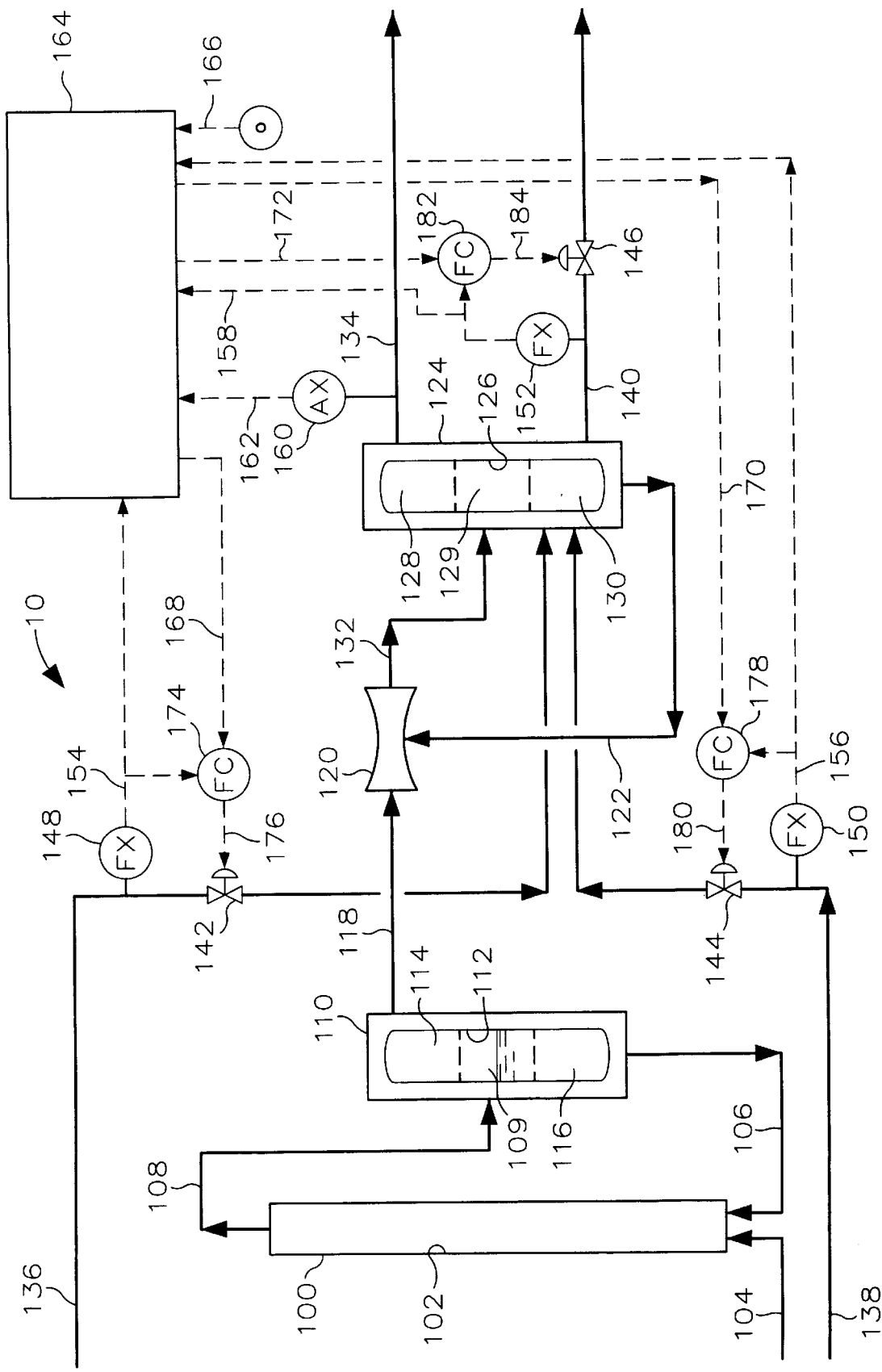

METHOD FOR REDUCING ORGANIC FLUORIDE LEVELS IN HYDROCARBONS

The present invention relates to a method and/or system for reducing the concentration of organic fluorides present in a hydrocarbon mixture. More particularly, the invention relates to a method and/or system for reducing the concentration of organic fluorides present in an alkylation reactor effluent.

BACKGROUND OF THE INVENTION

The use of catalytic alkylation processes to produce branched hydrocarbons having properties that are suitable for use as gasoline blending components is well known in the art. Generally, the alkylation of olefins by saturated hydrocarbons, such as isoparaffins, is accomplished by contacting the reactants with an acid catalyst to form a reaction mixture, settling the mixture to separate the catalyst from the hydrocarbons and further separating the alkylation reactor effluent, for example, by fractionation, to recover the separate product streams. Normally, the alkylation reactor effluent of the alkylation process contains hydrocarbons having five to ten carbon atoms per molecule, preferably seven to nine carbons atoms per molecule. In order to have the highest quality gasoline blending stock, it is preferred for the alkylate hydrocarbons formed in the alkylation process to be highly branched and contain seven to nine carbon atoms per molecule.

Recent efforts to improve conventional hydrogen fluoride catalyzed alkylation processes have resulted in the development of new catalyst compositions that contain hydrogen fluoride and a volatility reducing additive. These new catalyst compositions have been found to be quite effective as an alkylation catalyst and to provide many other favorable benefits. However, it has also been found that in the alkylation process that uses the catalyst mixture containing hydrogen fluoride and such additive there is an increase in the production of undesirable organic fluorides. In fact, as the concentration of hydrogen fluoride in the new catalyst composition becomes more dilute, the amount of organic fluorides produced in the alkylation process increases. Organic fluorides produced can include, but are not limited to, organic fluorides having in the range of from about 3 to about 14 carbon atoms per molecule. Typical organic fluorides produced can include, but are not limited to, 2-fluoropropane, 2-fluorobutane, 2-fluoro-2-methylpropane, 2-fluoropentane, 2-fluoro-2-methylbutane, 2-fluoro-3-methylbutane, methylfluorobutane isomers, 2-fluorohexane, 3-fluorohexane, methylfluoropentanes, dimethylfluorobutanes, fluoroheptanes, fluoromethylhexanes, dimethylfluoropentanes, fluorooctanes, fluoromethylheptanes, dimethylfluorohexanes, fluorotrimethylpentanes fluorononanes, fluoromethyloctanes, dimethylfluoroheptanes, fluorotrimethylhexanes.

In many instances, it is not desirable for the product streams to have an excessively high concentration of organic fluorides.

Therefore, development of an efficient process for reducing the level of organic fluorides present in a hydrocarbon mixture would be a significant contribution to the art.

BRIEF SUMMARY OF THE INVENTION

It is, thus, an object of the present invention to provide an improved process for reducing the level of at least one organic fluoride in a hydrocarbon mixture which is economical and efficient.

A further object of the present invention is to provide an improved system to be used in reducing the level of at least one organic fluoride in a hydrocarbon mixture which is economical in construction and reliable and efficient in operation.

A yet further object of the present invention is to provide an improved system to be used in reducing the level of at least one organic fluoride in a hydrocarbon mixture which includes means for controlling the level of at least one organic fluoride present in the hydrocarbon mixture and/or for controlling the research octane of the hydrocarbon mixture.

According to a first embodiment of the present invention, a method for decreasing the level of at least one organic fluoride present in a hydrocarbon mixture is provided. The method of the first embodiment comprises the steps of:

passing the hydrocarbon mixture to an eductor;

educting into the hydrocarbon mixture a catalyst comprising a volatility reducing additive and hydrofluoric acid to thereby form a hydrocarbon-catalyst mixture;

permitting the hydrocarbon-catalyst mixture to undergo a phase separation to thereby produce a hydrocarbon phase having a lower concentration of at least one organic fluoride than the hydrocarbon mixture and to thereby produce a catalyst phase;

withdrawing at least a portion of the catalyst phase for use as the catalyst; and withdrawing at least a portion of the hydrocarbon phase to form a hydrocarbon product stream.

According to a second embodiment of the present invention, a process for alkylating at least a portion of a hydrocarbon feedstock comprising olefins and isoparaffins is provided. The process of the second embodiment comprises the steps of:

introducing the hydrocarbon feedstock into an alkylation reaction zone;

contacting the hydrocarbon feedstock with a first catalyst comprising a volatility reducing additive and hydrofluoric acid in the alkylation reaction zone to thereby produce alkylation of at least a portion of the olefins and isoparaffins in the form of an alkylation reaction effluent;

passing the thus-produced alkylation reaction effluent from the alkylation reaction zone to a first settling zone and permitting a phase separation to occur so as to produce a first catalyst phase and to produce a first hydrocarbon phase having a concentration of at least one organic fluoride in the range of from about 150 ppmw to about 10,000 ppmw, based on the total weight of the first hydrocarbon phase, and having a research octane in the range of from about 85 to about 98; and contacting at least a portion of the first hydrocarbon phase with a second catalyst comprising a volatility reducing additive and hydrofluoric acid to thereby produce a hydrocarbon product stream having a lower concentration of at least one organic fluoride than the first hydrocarbon phase.

According to a third embodiment of the present invention, a system or apparatus is provided comprising:

an alkylation reactor;

a first settler, having an upper portion, an intermediate portion and a lower portion;

an eductor;

a second settler, having an upper portion, an intermediate portion and a lower portion;

first conduit means operably related to the alkylation reactor for introducing a hydrocarbon feedstock comprising olefins and isoparaffins into the alkylation reactor;

second conduit means operably related to the alkylation reactor for introducing a first catalyst comprising a volatility reducing additive and hydrofluoric acid into the alkylation reactor;

third conduit means operably related to the alkylation reactor and operably related to the first settler for withdrawing an alkylation reaction effluent from the alkylation reactor and for introducing the alkylation reaction effluent into the intermediate portion of the first settler, the upper portion of the first settler being operable for containing a first hydrocarbon phase separated from the alkylation reaction effluent and the lower portion of the first settler being operable for containing a first catalyst phase separated from the alkylation reaction effluent;

fourth conduit means operably related to the first settler and operably related to the eductor for withdrawing at least a portion of the first hydrocarbon phase from the upper portion of the first settler and for introducing the at least a portion of the first hydrocarbon phase into the eductor;

fifth conduit means, operably related to the second settler and operably related to the eductor for withdrawing at least a portion of a second catalyst phase comprising a volatility reducing additive and hydrofluoric acid from the lower portion of the second settler and for introducing the at least a portion of the second catalyst phase into the eductor for mixing with the at least a portion of the first hydrocarbon phase to thereby produce a hydrocarbon-catalyst mixture;

sixth conduit means operably related to the eductor and operably related to the second settler for withdrawing the hydrocarbon-catalyst mixture from the eductor and for introducing the hydrocarbon-catalyst mixture into the intermediate portion of the second settler, the upper portion of the second settler being operable for containing a second hydrocarbon phase separated from the hydrocarbon-catalyst mixture and the lower portion of the second settler being operable for containing the second catalyst phase separated from the hydrocarbon-catalyst mixture; and seventh conduit means operably related to the second settler for withdrawing at least a portion of the second hydrocarbon phase from the second settler to thereby form a hydrocarbon product stream.

Other objects and advantages will become apparent from the detailed description and the appended claims.

BRIEF DESCRIPTION OF THE DRAWING

The FIGURE is a schematic flow diagram presenting an embodiment of the present invention.

DETAILED DESCRIPTION OF THE INVENTION

According to the first embodiment of the present invention, the hydrocarbon mixture can comprise paraffins and/or olefins, wherein each of these hydrocarbons contains at least 3 carbon atoms per molecule. The hydrocarbon mixture further comprises at least one organic fluoride in the range of from about 150 ppmw to about 10,000 ppmw, based on the total weight of the hydrocarbon mixture. More typically, the concentration of the at least one organic fluoride is in the range of from about 200 ppmw to about 1,000 ppmw; and most typically from 250 ppmw to 500 ppmw, based on the total weight of the hydrocarbon mixture.

The research octane number (RON) of the hydrocarbon mixture is typically in the range of from about 85 to about 98, more typically from about 87 to about 96; and most typically from 89 to 94. RON, as used herein, is defined as the octane number of a hydrocarbon stream as determined using the ASTM D2699-97 method.

The hydrocarbon mixture is most suitably an alkylation reaction product produced from the alkylation of olefins having at least 3 carbon atoms per molecule with isoparaffins having at least 4 carbon atoms per molecule.

The hydrocarbon mixture can be contacted with a catalyst comprising a volatility reducing additive and hydrofluoric acid by any suitable manner, including mixing and blending. The volatility reducing additive can be any compound effective in reducing the volatility of a mixture resulting from the addition of the volatility reducing additive to hydrofluoric acid. More particularly, the volatility reducing additive can be a compound selected from the group consisting of sulfone, ammonia, methylamines, ethylamines, propylamines, butylamines, pentylamines, pyridine, alkylpyridines, picoline, melamine, hexamethylenetetramine and the like.

The sulfones suitable for use in this invention are the sulfones of the general formula $$R\text{—}SO_2\text{—}R^1$$

wherein R and $R^1$ are monovalent hydrocarbon alkyl or aryl substituents, each containing from 1 to 8 carbon atoms, and wherein R and $R^1$ can be the same or different. Examples of suitable sulfones include, but are not limited to, dimethylsulfone, di-n-propylsulfone, diphenylsulfone, ethylmethylsulfone and alicyclic sulfones wherein the $SO_2$ group is bonded to a hydrocarbon ring. In such a case, R and $R^1$ are forming together a branched or unbranched hydrocarbon divalent moiety preferably containing from 3 to 12 carbon atoms. Among the latter, tetramethylenesulfone or sulfolane, 3-methylsulfolane and 2,4-dimethylsulfolane are more particularly suitable since they offer the advantage of being liquid at process operating conditions of concern herein. These sulfones may also have substituents, particularly one or more halogen atoms, such as for example, chloromethylethylsulfone. These sulfones may advantageously be used in the form of mixtures of any two or more thereof. The most preferred volatility reducing additive is sulfone.

It is preferred to contact the hydrocarbon mixture with the catalyst by mixing in an eductor which can also be referred to as an ejector, siphon, exhauster or jet pump. As used herein, the operation and apparatus of the eductor are such to allow a pumping fluid to enter through a nozzle, pass through a venturi nozzle, and discharge through a discharge opening. As the pumping fluid passes into the venturi nozzle, it develops a suction that causes fluid in a suction chamber to be entrained with the pumping fluid stream and to be delivered through the discharge opening.

The hydrocarbon mixture is passed to the pumping fluid inlet of an eductor wherein the catalyst is educted into the hydrocarbon mixture to thereby produce a hydrocarbon-catalyst mixture. The hydrocarbon-catalyst mixture is then permitted to undergo a phase separation in a settler vessel thereby producing a hydrocarbon phase and a catalyst phase. The hydrocarbon phase has a lower concentration of at least one organic fluoride than the hydrocarbon mixture. More particularly, the concentration of at least one organic fluoride in the hydrocarbon phase is preferably in the range of from about 0 ppmw to about 1,000 ppmw; more preferably from about 0 ppmw to about 100 ppmw; and most preferably from 0 ppmw to 50 ppmw, based on the total weight of the hydrocarbon phase.

The RON of the hydrocarbon phase is preferably in the range of from about 85 to about 98, more preferably from about 87 to about 96, and most preferably from 89 to 94.

In addition, at least a portion of the catalyst phase can be used as the catalyst and at least a portion of the hydrocarbon phase is withdrawn from the process to form a hydrocarbon product stream.

The volatility reducing additive concentration of the catalyst is such as to provide a hydrocarbon phase having a lower concentration of at least one organic fluoride than the hydrocarbon mixture.

More particularly, the volatility reducing additive is present in the catalyst in an amount in the range of from exceeding about 0 weight percent to about 50 weight percent; preferably from about 5 weight percent to about 35 weight percent; and most preferably from 10 weight percent to 25 weight percent, based on the total weight of the catalyst.

The concentration of the volatility reducing additive in the catalyst can be varied so as to adjust and/or control the concentration of at least one organic fluoride in the hydrocarbon product stream and/or to adjust and/or control the RON of the hydrocarbon product stream.

More particularly, the concentration of the volatility reducing additive in the catalyst can be varied by replacing at least a portion of the catalyst phase with a makeup catalyst comprising a compound selected from the group consisting of the volatility reducing additive, hydrofluoric acid, and mixtures thereof.

The amount of volatility reducing additive can be adjusted such that the RON of the hydrocarbon product stream is controlled to a level in the range of from about 85 to about 98; preferably from about 87 to about 96; and most preferably from 89 to 94; and/or such that the concentration of the at least one organic fluoride present in the hydrocarbon product stream is controlled to a level in the range of from about 0 percent to about 65 percent; preferably from about 0 percent to about 50 percent; and most preferably from 0 percent to 25 percent of the concentration of the at least one organic fluoride of the hydrocarbon mixture.

According to the second embodiment of the present invention, the hydrocarbon feedstock can comprise iso-paraffins having at least 4 carbon atoms per molecule and olefins having at least 3 carbon atoms per molecule. Preferably, the iso-paraffins have in the range of from 4 to 5 carbon atoms per molecule and the olefins have in the range of from 3 to 4 carbon atoms per molecule.

The olefins contained in the hydrocarbon feedstock can be alkylated with the iso-paraffins by contacting the hydrocarbon feedstock, by any suitable manner in an alkylation reaction zone, with a first catalyst comprising hydrofluoric acid and a volatility reducing additive (as described above) to thereby produce alkylation of at least a portion of the olefins and iso-paraffins in the form of an alkylation reaction effluent comprising alkylate, unreacted iso-paraffins, the first catalyst, and, in runaway type situations, unreacted olefins.

The alkylation reaction effluent can be passed from the alkylation reaction zone to a first settling zone wherein a phase separation occurs. The phase separation produces a first hydrocarbon phase having a concentration of at least one organic fluoride in the range of from about 150 ppmw to about 10,000 ppmw; more particularly from about 200 ppmw to about 1,000 ppmw; and most particularly from 250 ppmw to 500 ppmw, based on the total weight of the first hydrocarbon phase; and the first hydrocarbon phase has a RON in the range of from about 85 to about 98; more particularly from about 87 to about 96; and most particularly from 89 to 94. The first hydrocarbon phase can comprise alkylate, unreacted iso-paraffins, and unreacted olefins.

The phase separation in the first settling zone also produces a first catalyst phase which can be used, at least in part, as the first catalyst. At least a portion of the first hydrocarbon phase can be contacted with a second catalyst comprising a volatility reducing additive and hydrofluoric acid by any suitable manner, including mixing and blending to thereby produce a hydrocarbon product stream. It is preferred to contact at least a portion of the first hydrocarbon phase with the second catalyst by mixing in an eductor.

At least a portion of the first hydrocarbon phase is passed to an eductor wherein the second catalyst is educted into at least a portion of the first hydrocarbon phase to thereby form a hydrocarbon-catalyst mixture. The hydrocarbon-catalyst mixture is then passed to a second settling zone wherein a phase separation occurs thereby producing a second hydrocarbon phase and a second catalyst phase. The second hydrocarbon phase has a lower concentration of at least one organic fluoride than the first hydrocarbon phase. More particularly, the concentration of at least one organic fluoride in the second hydrocarbon phase is preferably in the range of from about 0 ppmw to about 1,000 ppmw; more preferably from about 0 ppmw to about 100 ppmw; and most preferably from 0 ppmw to 50 ppmw, based on the total weight of the second hydrocarbon phase.

The second hydrocarbon phase has a RON in the range of from about 85 to about 98; preferably from about 87 to about 96; and most preferably from 89 to 94.

In addition, at least a portion of the second catalyst phase can be used as the second catalyst and at least a portion of the second hydrocarbon phase is withdrawn from the process to form a hydrocarbon product stream.

The volatility reducing additive concentration of the second catalyst is such as to provide the second hydrocarbon phase having a lower concentration of at least one organic fluoride than the first hydrocarbon phase. For best results in decreasing the concentration of at least one organic fluoride in the first hydrocarbon phase, the concentration of volatility reducing additive in the second catalyst is less than the concentration of volatility reducing additive in the first catalyst. More particularly, the volatility reducing additive is present in the second catalyst in an amount in the range of from exceeding about 0 weight percent to about 50 weight percent; preferably from about 5 weight percent to about 35 weight percent; and most preferably from 10 weight percent to 25 weight percent based on the total weight of the second catalyst.

The amount of volatility reducing additive present in the second catalyst can be varied in order to control at least one processing variable, such as, but not limited to, the concentration of at least one organic fluoride of the hydrocarbon product stream and/or the RON of the hydrocarbon product stream.

Where the processing variable is the concentration of at least one organic fluoride, the concentration of the volatility reducing additive present in the second catalyst can be decreased responsive to an increase in the concentration of at least one organic fluoride of the hydrocarbon product stream above a desired concentration of at least one organic fluoride of the hydrocarbon product stream to thereby decrease the concentration of at least one organic fluoride of the hydrocarbon product stream. Alternately, the concentration of the volatility reducing additive present in the second catalyst can be increased responsive to a decrease in the concentration of at least one organic fluoride in the hydrocarbon product stream below the desired concentration to thereby increase the concentration of at least one organic fluoride of the hydrocarbon product stream.

Where the processing variable is RON, the concentration of the volatility reducing additive present in the second catalyst can be decreased responsive to an increase in the RON of the hydrocarbon product stream above a desired RON of the hydrocarbon product stream to thereby decrease the RON of the hydrocarbon product stream. Alternately, the concentration of the volatility reducing additive present in the second catalyst can be increased responsive to a decrease in the RON of the hydrocarbon product stream below the desired RON to thereby increase the RON of the hydrocarbon product stream.

One skilled in the art can establish the concentration of the volatility reducing additive present in the second catalyst at a level which maximizes the RON of the hydrocarbon product stream, or, which minimizes the concentration of at least one organic fluoride of the hydrocarbon product stream, or, which reaches a desired balance between the RON and the concentration of at least one organic fluoride of the hydrocarbon product stream.

The desired concentration of at least one organic fluoride of the hydrocarbon product stream is preferably in the range of from about 0 percent to about 65 percent; more preferably from about 0 percent to about 50 percent; and most preferably from 0 percent to 25 percent of the concentration of at least one organic fluoride of the first hydrocarbon phase.

The desired RON of the hydrocarbon product stream is preferably in the range of from about 85 to about 98; more preferably from about 87 to about 96; and most preferably from 89 to 94.

For best results in decreasing the concentration of at least one organic fluoride in the first hydrocarbon phase, the ratio by weight of iso-butane to alkylate in the first hydrocarbon phase is in the range of from about 1:1 to about 8:1, preferably from about 1.5:1 to about 6:1; and most preferably from 2:1 to 5:1.

According to the third embodiment of the present invention, the system of the present invention will be described with reference to the drawing.

Referring to the FIGURE therein is illustrated the inventive system or apparatus 10 including an alkylation reactor 100 having an inside wall 102 which defines an alkylation reaction zone. The alkylation reactor 100 is operably related by connection in fluid flow communication to a conduit 104 providing first conduit means for introducing a hydrocarbon feedstock into the alkylation reaction zone. The alkylation reactor 100 is also operably related by connection in fluid flow communication to a conduit 106 providing second conduit means for introducing a first catalyst comprising a volatility reducing additive, as described above, and hydrofluoric acid into the alkylation reaction zone. The alkylation reactor 100 provides means for alkylating at least a portion of the hydrocarbon feedstock to thereby produce an alkylation reaction effluent.

The alkylation reactor 100 is operably related by connection in fluid flow communication to a conduit 108 providing third conduit means for removing the alkylation reaction effluent from alkylation reactor 100 and for introducing the alkylation reaction effluent into an intermediate portion 109 of a first settler 110. First settler 110 also has an inside wall 112 which defines a first settling zone, having an upper portion 114, intermediate portion 109 and a lower portion 116, for allowing a phase separation of the alkylation reaction effluent. The upper portion 114 of first settler 110 is operable for containing a first hydrocarbon phase separated from the alkylation reaction effluent and the lower portion 116 of first settler 110 is operable for containing a first catalyst phase separated from the alkylation reaction effluent.

The lower portion 116 of first settler 110 is operably related by connection in fluid flow communication, via conduit 106, with alkylation reactor 100 for returning the first catalyst phase to alkylation reactor 100 for use as the first catalyst.

The upper portion 114 of first settler 110 is operably related by connection in fluid flow communication to a conduit 118 providing fourth conduit means for withdrawing at least a portion of the first hydrocarbon phase from upper portion 114 of first settler 110 and for introducing at least a portion of the first hydrocarbon phase into an eductor 120. Eductor 120 is operably related by connection in fluid flow communication via conduit 122 with a second settler 124 having an inside wall 126 which defines a second settling zone having an upper portion 128, an intermediate portion 129 and a lower portion 130. Conduit 122 provides fifth conduit means for withdrawing at least a portion of a second catalyst phase comprising a volatility reducing additive and hydrofluoric acid from the lower portion 130 of second settler 124 and for introducing at least a portion of the second catalyst phase into eductor 120 for mixing with at least a portion of the first hydrocarbon phase introduced via conduit 118 into eductor 120 to thereby produce a hydrocarbon-catalyst mixture.

Eductor 120 is operably related by connection in fluid flow communication to a conduit 132 which provides sixth conduit means for withdrawing the hydrocarbon-catalyst mixture from eductor 120 and for introducing the hydrocarbon-catalyst mixture into the intermediate portion 129 of second settler 124. The upper portion 128 of second settler 124 is operable for containing a second hydrocarbon phase separated from the hydrocarbon-catalyst mixture and the lower portion 130 of the second settler 124 is operable for containing the second catalyst phase separated from the hydrocarbon-catalyst mixture.

Upper portion 128 of second settler 124 is operably related by connection in fluid flow communication to a conduit 134 which provides seventh conduit means for withdrawing at least a portion of the second hydrocarbon phase from upper portion 128 of second settler 124 to thereby form a hydrocarbon product stream.

In addition, the inventive system or apparatus 10 can include a control system operably related to second settler 124 which provides control means for varying the concentration of the volatility reducing additive present in the second catalyst phase in order to control at least one processing variable of the hydrocarbon product stream.

Dash lines, which designate signal lines in the drawings, are electrical or pneumatic in this preferred embodiment. However, the invention is also applicable to mechanical, hydraulic, or other signal means for transmitting information. In almost all control systems some combination of these types of signals will be used. However, the use of any other type of signal transmission, compatible with the process and equipment in use, is within the scope of the invention.

A digital computer is used in the preferred embodiment of this invention to calculate the required control signal based on measured process parameters as well as set points supplied to the computer. Any computer control system having software that allows operation in a real time environment for reading values of external variables and transmitting signals is suitable for use in this invention.

Signal lines are also utilized to represent the results of calculations carried out in a digital computer and the term "signal" is utilized to refer to such results. Thus, the term signal is used not only to refer to electrical currents or pneumatic pressures but is also used to refer to binary representations of a calculated or measured value.

The controllers shown may utilize the various modes of control such as proportional, proportional-integral, proportional-derivative, or proportional-integral-derivative. In this preferred embodiment, proportional-integral-derivative controllers are utilized but any controller capable of accepting two input signals and producing a scaled output signal, representative of a comparison of the two input signals, is within the scope of the invention.

The scaling of an output signal by a controller is well known in control system art. Essentially, the output of a controller may be scaled to represent any desired factor or variable. An example of this is where a desired flow rate and an actual flow rate are compared by a controller. The output could be a signal representative of a desired change in the flow rate of some liquid necessary to make the desired and actual flows equal. On the other hand, the same output signal could be scaled to represent a percentage or could be scaled to represent a temperature change required to make the desired and actual flows equal. If the controller output can range from 0 to 10 volts, which is typical, then the output signal could be scaled so that an output signal having a voltage level of 5.0 volts corresponds to 50 percent of some specified flow rate.

The various transducing means used to measure parameters which characterize the process and the various signals generated thereby may take a variety of forms or formats. For example, the control elements of the system can be implemented using electrical analog, digital electronic, pneumatic, hydraulic, mechanical or other similar types of equipment or combinations of one or more such equipment types. While the presently preferred embodiment of the invention preferably utilizes a combination of pneumatic final control elements in conjunction with electrical analog signal handling and translation apparatus, the apparatus and method of the invention can be implemented using a variety of specific equipment available to and understood by those skilled in the process control art.

Likewise, the format of the various signals can be modified substantially in order to accommodate signal format requirements of the particular installation, safety factors, the physical characteristics of the measuring or control instruments and other similar factors. For example, a raw flow measurement signal produced by a differential pressure orifice flow meter would ordinarily exhibit a generally proportional relationship to the square of the actual flow rate. Other measuring instruments might produce a signal which is proportional to the measured parameter, and still other transducing means may produce a signal which bears a more complicated, but known, relationship to the measured parameter. Regardless of the signal format or the exact relationship of the signal to the parameter which it represents, each signal representative of a measured process parameter or representative of a desired process value will bear a relationship to the measured parameter or desired value which permits designation of a specific measured or desired value by a specific signal value. A signal which is representative of a process measurement or desired process value is therefore one from which the information regarding the measured or desired value can be readily retrieved regardless of the exact mathematical relationship between the signal units and the measured or desired process units.

Referring again to the FIGURE, the control system comprises a conduit 136 which is operably related by connection in fluid flow communication to lower portion 130 of second settler 124. Conduit 136 provides an eighth conduit means for introducing a hydrofluoric acid stream into the second catalyst phase, and a conduit 138 which is operably related by connection in fluid flow communication to lower portion 130 of second settler 124 provides a ninth conduit means for introducing a volatility reducing additive stream into the second catalyst phase. The hydrofluoric acid stream in conduit 136 can be combined with the volatility reducing additive stream in conduit 138 prior to introduction into the second catalyst phase contained in lower portion 130 of second settler 124. A conduit 140 is operably related by connection in fluid flow communication to lower portion 130 of second settler 124 and provides tenth conduit means for withdrawing a purge stream from the second catalyst phase.

Conduit 136 is operably related to a first control valve 142 interposed therein which provides first control valve means for adjusting the flow rate of the hydrofluoric acid stream through conduit 136. Conduit 138 is operably related to a second control valve 144 interposed therein which provides second control valve means for adjusting the flow rate of the volatility reducing additive stream through conduit 138. Conduit 140 is operably related to a third control valve 146 interposed therein which provides third control valve means for adjusting the flow rate of the purge stream through conduit 140.

Operably associated with each of the conduits 136, 138 and 140 is a respective flow transducer 148, 150 and 152, each of which produces a respective flow signal 154, 156 and 158 which is representative of the volume flow rate of the material carried through the conduits with which it is associated. Flow transducers 148, 150 and 152 can comprise flow measuring devices, such as orifice plates, located within conduits 136, 138 and 140, respectively, for measuring the volume flow rates.

Analyzer 160, which is preferably a chromatograph, provides means for establishing a processing variable signal 162 representative of the actual value of at least one processing variable of the hydrocarbon product stream. Analyzer 160 is preferably adapted to take a sample of fresh hydrocarbon product stream from conduit 134 and to deliver, in response to the analysis of the hydrocarbon product stream, processing variable signal 162 which is representative of the actual value of the at least one processing variable of the hydrocarbon product stream. Analyzer 160 can include off-line analysis of the sample of the hydrocarbon product stream.

A computer calculation block 164, preferably associated with a distributed control system, receives as inputs thereto the flow rate signals 154, 156 and 158, processing variable signal 162 and an operator entered signal 166 which is representative of the desired value for the at least one processing variable of the hydrocarbon product stream flowing in conduit 134. Computer calculation block 164 establishes output signals 168, 170 and 172, each responsive to signals 154, 156 and 158 and to the difference between signals 162 and 166. Signals 168, 170 and 172 are scaled to be representative of the flow rates of the hydrofluoric acid stream in conduit 136, the volatility reducing additive stream in conduit 138 and the purge stream in conduit 140, respectively, required to maintain the actual value of the at least one processing variable represented by signal 162 substantially equal to the desired value of the at least one processing variable represented by signal 166.

Signal 168 is provided as a set point input to flow controller 174. Also provided as a processing variable input to flow controller 174 is flow rate signal 154 which is representative of the actual flow rate of hydrofluoric acid in conduit 136. Flow controller 174 provides an output signal 176 which is responsive to the difference between signals 168 and 154. Signal 176 is scaled to be representative of the position of first control valve 142 required to maintain the flow rate represented by signal 154 substantially equal to the flow rate represented by signal 168.

Signal 170 is provided as a set point input to flow controller 178. Also provided as a processing variable input to flow controller 178 is flow rate signal 156 which is representative of the actual flow rate of the volatility reducing additive in conduit 138. Flow controller 178 provides an output signal 180 which is responsive to the difference between signals 170 and 156. Signal 180 is scaled to be representative of the position of second control valve 144 required to maintain the flow rate represented by signal 156 substantially equal to the flow rate represented by signal 170.

Signal 172 is provided as a set point input to flow controller 182. Also provided as a processing variable input to flow controller 182 is flow rate signal 158 which is representative of the actual flow rate of the purge stream in conduit 140. Flow controller 182 provides an output signal 184 which is responsive to the difference between signals 172 and 158. Signal 184 is scaled to be representative of the position of third control valve 146 required to maintain the flow rate represented by signal 158 substantially equal to the flow rate represented by signal 172.

The following example is provided to further illustrate this invention and is not to be considered as unduly limiting the scope of this invention.

EXAMPLE

This example illustrates the use of catalysts comprising hydrofluoric acid and a volatility reducing additive in the reduction of organic fluoride levels in a hydrocarbon mixture.

A reactor was constructed to enable the steady-state evaluation of HF/sulfolane catalysts comprising varying levels of hydrofluoric acid and sulfolane. The reactor was a section of monel schedule 40 pipe 2 feet in length and 1 inch in diameter connected at one end to a monel sight gauge via ¼" monel tubing, and connected at the other end to a feed introduction nozzle, having a 0.01 inch diameter orifice, via ⅛" monel tubing.

The catalyst was circulated through the reactor and monel sight gauge at a flow rate in the range of from about 50 mL/min to about 100 mL/min. The catalyst composition was varied for each run, as shown in the Table. A hydrocarbon feed comprising a 2/1 by weight mixture of isobutane/alkylate was blended into a feed cylinder. The alkylate was obtained from an alkylation unit of a refinery. For each run, the hydrocarbon feed was pumped through the feed introduction nozzle into the reactor at a rate of about 300 mL/hour. The reactor effluent flowed into the monel sight gauge wherein the hydrocarbon product and any catalyst carryover were separated.

The hydrocarbon product was drawn off into a suitable sample cylinder, passed over alumina at an ambient temperature (to adsorb free HF), collected, and analyzed by standard gas chromatography using a GC sample injection valve so that no light materials were lost. Test data results for each run are summarized in the Table.

TABLE

| | | | Catalyst Comp. (1, 2) | | | | | |
|---|---|---|---|---|---|---|---|---|
| | | TOS | | | | | | |
| | Temp. (°F.) | Cumulative (hrs.) | % HF | % Sulfolane | 2FP (ppm) | 2FP (conv) | RON | RON (Δ) |
| Feed | — | — | — | — | 2345 | — | 91.7 | — |
| Run 1 (inventive) | 95.7 | 23.0 | 64.3 | 25.0 | 192 | 91.8 | 91.7 | 0 |
| Run 2 (inventive) | 95.9 | 27.3 | 68.9 | 21.0 | 84 | 96.4 | 91.4 | −0.3 |
| Run 3 (inventive) | 95.5 | 47.0 | 72.9 | 18.0 | 82 | 96.5 | 91.3 | −0.4 |
| Run 4 (inventive) | 95.5 | 50.3 | 76.1 | 15.0 | 37 | 98.2 | 91.3 | −0.4 |
| Run 5 (inventive) | 95.9 | 73.5 | 78.4 | 12.0 | 0 | 100 | 91.1 | −0.6 |
| Run 6 (control) | 97.3 | — | 91.2 | 0 | 0 | 100 | 90.6 | −1.1 |

1-All catalysts contain 1–2% water by weight.
2-Balance of the catalyst compositions comprise acid soluble oil and dissolved light hydrocarbons.
2FP = 2-fluoropropane
TOS = Time on stream The test data presented in the Table show that use of catalysts comprising hydrofluoric acid and sulfolane in Runs 1 through 5 significantly reduced the level of 2-fluoropropane contained in the hydrocarbon feed with less degradation in RON of the hydrocarbon product than that of control Run 6 in which the catalyst contained no sulfolane.

It is noted that the use of 12% by weight sulfolane in the catalyst in inventive Run 5 resulted in 100% conversion of 2-fluoropropane and a RON of the hydrocarbon product of 91.1 as compared to control Run 6 where the 2-fluoropropane conversion was also 100% but the RON was only 90.6.

Reasonable variations, modifications, and adaptations can be made within the scope of the disclosure and the appended claims without departing from the scope of this invention.

That which is claimed is:

1. A method for decreasing the level of organic fluorides present in a hydrocarbon mixture comprising an alkylation reaction product produced from the alkylation of an olefin with an isoparaffin, said method comprising the steps of:

passing said hydrocarbon mixture to an eductor;

educting into said hydrocarbon mixture a catalyst comprising a volatility reducing additive and hydrofluoric acid to thereby form a hydrocarbon-catalyst mixture;

permitting said hydrocarbon-catalyst mixture to undergo a phase separation to thereby produce a hydrocarbon phase having a lower concentration of at least one organic fluoride than said hydrocarbon mixture and to thereby produce a catalyst phase;

withdrawing at least a portion of said catalyst phase for use as said catalyst; and withdrawing at least a portion of said hydrocarbon phase to form a hydrocarbon product stream.

2. A method as recited in claim 1 wherein said volatility reducing additive is a compound selected from the group consisting of sulfone, ammonia, methylamines, ethylamines, propylamines, butylamines, pentylamines, pyridine, alkylpyridines, melamine, hexamethylene-tetramine, and mixtures of any two or more thereof.

3. A method as recited in claim 1 wherein said volatility reducing additive is sulfone.

4. A method as recited in claim 1 wherein said volatility reducing additive is present in said catalyst in an amount in the range of from exceeding about 0 weight percent to about 50 weight percent based on the total weight of said catalyst.

5. A method as recited in claim 1 further comprising the step of replacing at least a portion of said catalyst phase with a makeup catalyst comprising a compound selected from the group consisting of a volatility reducing additive, hydrofluoric acid, and mixtures thereof.

* * * * *